United States Patent
Zheng et al.

(10) Patent No.: US 6,218,571 B1
(45) Date of Patent: Apr. 17, 2001

(54) 8-(ANILINO)-1-NAPHTHALENESULFONATE ANALOGS

(75) Inventors: Xiaoling Zheng, Fremont; Yeung Siu Yu, Pleasanton; Adva Yani, Milpitas; Paing C. Huang, San Francisco, all of CA (US)

(73) Assignee: LifeScan, Inc., Milpitas, CA (US)

( * ) Notice: Subject to any disclaimer, the term of this patent is extended or adjusted under 35 U.S.C. 154(b) by 0 days.

(21) Appl. No.: 09/428,296

(22) Filed: Oct. 27, 1999

(51) Int. Cl.$^7$ .................................................. C07C 309/00
(52) U.S. Cl. ............................................................. 562/61
(58) Field of Search ................................................. 562/61

(56) References Cited

U.S. PATENT DOCUMENTS

| | | | |
|---|---|---|---|
| 4,935,346 | 6/1990 | Phillips et al. | 435/14 |
| 4,962,040 | * 10/1990 | Hugl et al. | |
| 5,453,360 | 9/1995 | Yu | 435/28 |
| 5,563,031 | 10/1996 | Yu | 435/4 |
| 5,776,719 | 7/1998 | Douglas et al. | 435/28 |
| 5,922,530 | 7/1999 | Yu | 435/4 |

OTHER PUBLICATIONS

Kosower, Edward M., et al., "Intramolecular Donor–Acceptor Systems. 10. Multiple Fluorescences from 8–(Phenylamino)–1–Naphthalenesulfonates," *Journal of American Chemical Society* (1983) vol. 105:6236–6243.

* cited by examiner

Primary Examiner—Gary Geist
Assistant Examiner—John N Calve
(74) Attorney, Agent, or Firm—Bret E. Field; Bozicevic, Field & Francis LLP

(57) ABSTRACT

8-(anilino)-1-naphthalenesulfonate (ANS) analogs and methods for their use in analyte detection assays are provided. The subject ANS analogs are characterized by having at least one non-hydrogen substituent on their phenyl moiety and producing a reaction product with 3-methyl-2-benzothiazolinone hydrazone hydrchloride (MBTH) or an analog thereof, e.g. MBTHSB, that exhibits reduced drift. In certain preferred embodiments, the subject ANS analogs are described by the formula:

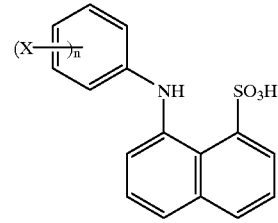

wherein: n is 1 to 5; and X is a substituent other than H. The subject ANS analogs find use in a variety of applications, particularly in analyte detection assays, such as glucose detection assays.

38 Claims, No Drawings

8-(ANILINO)-1-NAPHTHALENESULFONATE ANALOGS

FIELD OF THE INVENTION

The field of this invention is dye compositions, particularly dye compositions suitable for use in analyte detection assays, e.g. glucose detection assays.

BACKGROUND OF THE INVENTION

Analyte detection in physiological fluids, e.g. blood or blood derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include glucose for diabetes management, cholesterol, and the like. In response to this growing importance of analyte detection, a variety of analyte detection protocols and devices for both clinical and home use have been developed.

Many of the protocols and devices that have been developed to date employ a signal producing system to identify the presence of the analyte of interest in a physiological sample, such as blood. For example, one glucose detection system employed today uses a signal producing system that includes glucose oxidase, horseradish peroxidase, meta[3-methyl-2-benzothiazolinone hydrazone]N-sulfonyl benzenesulfonate monosodium (MBTHSB) and 8-(anilino)-1-naphthalenesulfonate (ANS). See U.S. Pat. No. 5,563,031. When glucose is combined with the above signal producing system in the presence of oxygen, the following reaction takes place:

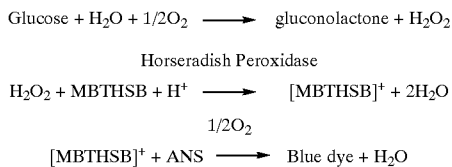

Despite the good results that have been achieved with the MBTHSB-ANS dye couple as described above, there is room for improvement in this system. For example, the blue dye product produced by the above described MBTHSB/ANS dye couple signal producing system is subject to drift during the detection phase of the assay, which ultimately can cause inaccuracy in the results.

Accordingly, there is continued interest in the development of new compounds for use in signal producing systems for analyte detection. Of particular interest would be the development of an ANS substitute that would yield a blue reaction product that is not subject to drift during detection.

Relevant Literature

Patents of interest include: U.S. Pat. Nos. 4,935,346; 4,962,040; 5,453,360; 5,563,031; 5,776,719; and 5,922,530. Also of interest is: Kosower & Kanety, "Intramolecular Donor-Acceptor Systems. 10. Multiple Fluorescences from 8-(phenylamino)-1-naphthalenesulfonates," J. Am. Chem. Soc. (1983) 105: 6236–6243.

SUMMARY OF THE INVENTION

ANS analogs and methods for their use are provided. The ANS analogs react with 3-methyl-2-benzothiazolinone hydrazone hydrochloride (MBTH) or analogs thereof, e.g. MBTHSB, to produce a reaction product that exhibits reduced drift as compared to the reaction product of ANS and MBTH, or the same MBTH analog. The subject ANS analogs are further characterized by having at least one non-hydrogen substituent present on their phenyl moiety. The subject analogs find use in a variety of applications and are particularly suited for use in analyte detection assays, such as glucose detection assays.

DESCRIPTION OF THE SPECIFIC EMBODIMENTS

The subject invention provides novel ANS analogs. The subject ANS analogs are characterized by having at least one non-hydrogen substituent present on their phenyl moieties. The presence of this at least one non-hydrogen substituent provides for reduced drift (as defined below) in the reaction product of the subject analogs with MBTH (or analogs thereof). Also provided are methods of using the subject ANS analogs in analyte detection assays, e.g. glucose detection assays. In further describing the subject invention, the subject analogs will be described first, followed by a discussion of the methods of using the subject analogs in analyte detection assays.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, singular references include the plural, unless the context clearly dictates otherwise. Unless defined otherwise, all technical and scientific terms used herein have the same meaning as commonly understood to one of ordinary skill in the art to which this invention belongs.

ANS Analogs

The invention provides novel ANS analogs. The subject ANS analogs are characterized in that they react with MBTH or analogs thereof in the presence of an oxidizing agent, a peroxidase and oxygen to produce a chromogenic, specifically a blue, reaction product that exhibits reduced drift. By "reduced drift" is meant that the reaction product produced upon combination of the subject ANS analog with MBTH (or an analog thereof) has a more stable reading compared with the reading drift observed upon reaction of ANS with MBTH, or the same MBTH analog, where the drift is measured over a period of 2 minutes from the start of the reaction. See the Experimental Section, infra, for a detailed protocol for measuring reading drift. The reading drift of the reaction products produced by the subject analogs is generally reduced by at least about 35%, usually at least about 60% and in many embodiments at least about 80%. Furthermore, the color yield provided by the reaction product produced by the subject analogs is often greater than that observed for ANS in many embodiments of the subject invention, where when the color yield is greater, the color yield can be at least 5% greater, usually at least about 20% and in many embodiments at least about 35% greater. Color yield is determined according to the protocol provided in the Experimental Section, infra.

The subject ANS analogs are characterized by having at least one non-hydrogen substituent present on their phenyl moieties. The number of non-hydrogen substituents present on the phenyl moiety may range from about 1 to 5, usually from about 1 to 3 and more usually from about 1 to 2. Any convenient non-hydrogen group may be employed as the substituent on the phenyl group, so long as it provides for an ANS analog that exhibits the above described reduced drift characteristics. Generally, the non-hydrogen substituent(s) will reduce the aggregation tendencies of the dye product produced by the analog with MBTH (or analogs thereof). Representative non-hydrogen substituents include: alkyls (substituted and/or branched), aryls (substituted or unsubstituted), halogens, OR, SeR, SR and $SiR_3$ where R is an alkyl or aryl group that may be substituted and/or branched.

Of particular interest are alkyl substituents, particularly lower alkyl substituents of I to 6 carbon atoms, usually 1 to 4 carbon atoms, where the alkyl substituents may be straight chained or branched. Alkyl substituents of particular interest include: methyl, isopropyl and tert-butyl.

In certain embodiments, the subject analogs are further limited in that when the substituent on the phenyl moiety is a methyl group, it is not bonded to the 3', 4' or 5' position of the phenyl moiety.

In many embodiments, the subject analogs are described by the structural formula:

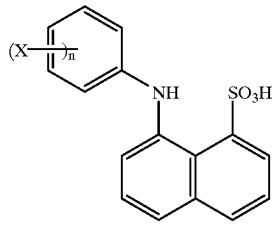

wherein:
n is an integer from 1 to 5, usually 1 to 3 and more usually 1 to 2;
and each X is independently a non-hydrogen substituent, where suitable substituents include those identified supra, where in many embodiments each X is an alkyl, typically a lower alkyl of 1 to 6, usually 1 to 4 carbon atoms, either straight chained or branched. As discussed above, in certain preferred embodiments, each X is either methyl, isopropyl or tert-butyl. In certain embodiments, if X is methyl, it is not located at the 3', 4' or 5' position of the phenyl moiety.

Of particular interest are the following ANS analogs: 8-(4'-tert-butylphenyl)amino-1-naphthalenesulfonate; 8-(4'-isopropylphenyl)amino-1-naphthalenesulfonate; 8-(2'-tert-butylphenyl)amino-1-naphthalenesulfonate; 8-(3',5'-di-tert-butylphenyl)amino-1-naphthalenesulfonate; 8-(4'-methylphenyl)amino-1-naphthalenesulfonate; and 8-(2'-methylphenyl)amino-1-naphthalenesulfonate.

Of interest are the subject analogs in either their acid or salt form, where cations present in the salt form include: ammonium, sodium, potassium, calcium, magnesium, and the like.

The above described ANS analogs of the subject invention may be prepared using any convenient protocol, where representative suitable protocols are provided in the Experimental section, infra.

Utility

The subject ANS compounds (either acid or salt form) find use in a variety of different applications as indicators for the presence of oxidizing agents. In other words, the subject analogs find use as reagent members of signal producing systems which detect the presence of oxidizing agents.

Oxidizing agents that may be detected using signal producing systems that include the subject analogs include: peroxides, e.g. hydrogen peroxide, cumene hydrogen peroxide, urea hydrogen peroxide, benzoyl peroxide; perborates, e.g. sodium, potassium; etc.

The subject analogs are particularly suited for use as reagents in signal producing systems designed to detect the presence of an analyte in a sample, usually a physiological sample, e.g. blood or a blood product derived from whole blood. Analytes of interest that may be detected using signal producing systems that include the subject analogs include: glucose, cholesterol, uric acid, alcohols (e.g. methanol, ethanol), formaldehyde, glycerol-3-phosphate, and the like. Of particular interest is the use of the subject analogs in signal producing systems designed to detect the presence of glucose in a physiological sample, particularly whole blood.

The signal producing systems of which the subject analogs are members typically further include: an oxidase, a peroxidase and a second member of a dye couple (in which one of the subject ANS analogs is the first member). The oxidase that is present in the signal producing system is generally chosen depending on the nature of the analyte to be detected, where suitable oxidases include: glucose oxidase, cholesterol oxidase, uricase, alcohol oxidase, aldehyde oxidase, glycerophosphate oxidase, and the like. Peroxidases that may be members of the signal producing system include: horseradish peroxidase, other enzymes and synthetic analogs having peroxidative activity or oxidizing chemicals and the like. See e.g., Y. Ci, F. Wang; Analytica Chimica Acta, 233 (1990), 299–302.

The second member of the dye couple of the signal producing system, of which the subject ANS analogs are the first member, is generally MBTH or an analog thereof. Suitable MBTH analogs that may be employed as members of the subject signal producing systems include those described in U.S. Pat. Nos. 5,922,530; 5,776,719; 5,563,031; 5,453,360 and 4,962,040, the disclosures of which are herein incorporated by reference. Of particular interest are the following MBTH analogs: meta[3-methyl-2-benzothiazolinone hydrazone]N-sulfonyl benzenesulfonate monosodium(MBTHSB), 3-methyl-2-benzothiazolinone hydrazone hydrochloride(MBTH), 3-methyl-6-(sodium sulfonate)benzothiazolinone-2-hydrazone, 6-hydroxy-3-methyl-2-benzothiazolinone hydrazone, 4-hydroxy-3-methyl-2-benzothiazolinone hydrazone, and 6-carboxyl-3-methyl-2-benzothiazolinone hydrazone.

In detecting an analyte by using a signal producing system of which the subject analogs are members, particularly members of a dye couple, as discussed above, a sample suspected of comprising the analyte of interest (i.e. the target analyte), usually a physiological sample, e.g. whole blood or a blood derived product, is contacted with the members of the signal producing system, either sequentially or at the same time. The presence of analyte results in the production of an oxidizing species, such as hydrogen peroxide, and a chromogenic reaction product is produced by covalent bonding of the two dye couple members of the above described signal producing system. The chromogenic reaction product is generally a blue reaction product, which is characterized by low drift in certain assay configurations (e.g. the SureStep® assay configuration) as described above. The presence of the chromogenic product is then related to the presence of analyte in the initial sample, where one may make qualitative or quantitative determinations of the amount of analyte in the original sample.

Signal producing systems comprising the subject analogs are particularly suited for use in analyte detection assay devices in which the members of the signal producing system are present on a porous support, e.g. a strip, onto which the sample is placed and from which the signal is read. Representative devices in which the subject analogs find use include those described in: U.S. Pat. Nos. 4,734,360; 4,900,666; 4,935,346; 5,059,394; 5,304,468; 5,306,623; 5,418,142; 5,426,032; 5,515,170; 5,526,120; 5,563,042; 5,620,863; 5,753,429; 5,573,452; 5,780,304; 5,789,255; 5,843,691; 5,846,486; and the like, the disclosures of which are herein incorporated by reference.

The following examples are offered by way of illustration and not by way of limitation.

EXPERIMENTAL

I. Synthesis of ANS Analogs

A. 4'-tert-Butyl ANS ammonium salt 8-Amino-1-naphthalenesulfonic acid (1.53 g), 4'-tert-butyl aniline (3.60 g) and 2,6-diethylaniline-HCl salt (0.95 g) were mixed in a Teflon vessel, and the vessel was sealed after it was purged with $N_2$. The vessel was then enclosed in a Parr bomb, and the bomb was placed in an oven and heated at 165° C. for 18 hrs. The mixture was re-stirred and heated for an additional 15 hrs. After the reaction was complete, the bomb was cooled in an ice bath. The mixture was transferred to a beaker and dissolved in ethyl acetate. Purification was done by chromatography (A column packed with Silica Gel 60 $GF_{254}$) with ethyl acetate as the eluent. Preparation of 4'-tert-butyl ANS ammonium salt: 4'-tert-butyl ANS was dissolved in a mixed solvent of ethanol and ethyl acetate. Aqueous $NH_4OH$ solution was added to the compound and the solvent was evaporated to give light yellow crystalline solids. Some dark red impurity was removed by rinsing the solid product with ethanol.

B. 4'-Isopropyl ANS ammonium salt 8-Amino-1-naphthalenesulfonic acid (1.53 g), 4'-isopropylaniline (3.60 g) and 2,6-diethylaniline-HCl salt (0.95 g) were mixed in a Teflon vessel, and the vessel was sealed after it was purged with $N_2$. The vessel was then enclosed in a Parr bomb, and the bomb was placed in an oven and heated at 165° C. for 18 hrs. The mixture was re-stirred and heated for an additional 15 hrs. After the reaction was complete, the bomb was cooled in an ice bath. The mixture was transferred to a beaker with the help of 2-propanol rinse. (Normally, a significant amount of crystalline product was observed which could be re-crystallized to the corresponding ammonium salt). Purification was done by chromatography (a column packed with Silica Gel 60 $GF_{254}$) with ethyl acetate as the eluent. Preparation of 4'-Isopropyl ANS ammonium salt: 4'-Isopropyl ANS was dissolved in a mixed solvent of ethanol and ethyl acetate. Aqueous $NH_4OH$ solution was added to the compound and the solvent was evaporated to give light yellow crystalline solids. Some dark red impurity was removed by rinsing the solid product with ethanol.

C. 2'-tert-Butyl ANS ammonium salt 8-Amino-1-naphthalenesulfonic acid (1.53 g), 2'-tert-butyl aniline (3.60 g) and 2,6-diethylaniline-HCl salt (0.95 g) were mixed in a Teflon vessel, and the vessel was sealed after it was purged with $N_2$. The vessel was then enclosed in a Parr bomb, and the bomb was placed in an oven and heated at 195° C. for 48 hrs. The mixture was re-stirred and heated for an additional 48 hrs. After the reaction was complete, the reaction was cooled in an ice bath. The mixture was transferred to a beaker and dissolved in ethyl acetate. Purification was done by chromatography (a column packed with Silica Gel 60 $GF_{254}$) with ethyl acetate as the solvent. Preparation of 2'-tert-butyl ANS ammonium salt: 2'-tert-butyl ANS was dissolved in a mixed solvent of ethanol and ethyl acetate. Aqueous $NH_4OH$ solution was added to the compound and the solvent was evaporated to give light yellow crystalline solids. Some dark red impurity was removed by rinsing the solid product with ethanol.

D. 3',5'-Di-tert-butyl ANS ammonium salt 8-Amino-1-naphthalenesulfonic acid (1.53 g), 3', 5'-di-tert-butyl aniline (3.80 g) and 2,6-diethylaniline-HCl salt (0.95 g) were mixed in a Teflon vessel, and the vessel was sealed after it was purged with $N_2$. The vessel was then enclosed in a Parr bomb, and the bomb was placed in an oven and heated at 190° C. for 24 hrs. The mixture was re-stirred and heated for an additional 24 hrs. After the reaction was complete, the bomb was cooled in an ice bath. The mixture was transferred to a beaker and dissolved in ethyl acetate. Purification was done by chromatography (a column packed with Silica Gel 60 $GF_{254}$) with ethyl acetate as the solvent.

Preparation of (3, 5'-Di-tert-butyl) ANS ammonium salt: (3, 5'-Di-tert-butyl) ANS was dissolved in a mixed solvent of ethanol and ethyl acetate. Aqueous $NH_4OH$ solution was added to the compound and the solvent was evaporated to give light yellow crystalline solids.

II. Testing of ANS analogs

The above synthesized ANS analogs were tested as follows:

A. Preparation of Test Strips

The porous side of a 0.351 μm polysulfone membrane (reaction matrix—obtained from U.S. Filter, San Diego, Calif.) is submerged in the aqueous dip shown in Table 1 until saturated. It is removed from the dip and the excess reagent is squeezed off with a glass rod. The strip is then hung inside an air circulating oven at 56° C. for about 10 minutes, after which time the strip is removed and dipped into the organic dip described in Table 2 until saturated. It is then dried again as in the previous step. The resulting strip is fashioned into the desired shape for testing.

TABLE 1

| Ingredient | Amount |
| --- | --- |
| $H_2O$ | 25 mL |
| Citric Acid | 282 mg |
| Trisodium Citrate | 348 mg |
| Mannitol | 250 mg |
| EDTA | 21 mg |
| Gantrez (obtained from GAF, New York, New York) | 112.5 mg |
| Crotein (obtained from CRODA, New York, New York) | 360 mg |
| Glucose Oxidase (126 U/mg) | 234.5 mg |
| Horse Radish Peroxidase (505 U/mg) | 62 mg |
| Carbapol 910 (0.11 mg/mL in acetonitrile) (obtained from BF Goodrich Clevelend Ohio) | 1.25 mL |
| 0.1M disodium citrate | 3.75 mL |

TABLE 2

| Ingredient | Amount |
| --- | --- |
| MeOH/EtOH/$H_2O$ (17.5/52.5/30) | 9.54 mL |
| MBTHSB Meta[3-methyl-2-benzothiazolinone hydrazone]N-sulfonyl benzenesulfonate monosodium | 38.8 mg |
| ANS or ANS analogs described above | 0.17 mmol |

TABLE 2-continued

| Ingredient | Amount |
| --- | --- |
| MAPHOS 60A (20% in the above solvent) (PPG/Mazer, Gurnee, Illinios) | 0.46 mL |

B. Testing

SureStep® strip configurations were used for testing of glucose response. Testing was conducted in an environmental chamber at 35° C. and 50% relative humidity. Reflectance data was collected on modified SureStep® meters. Blood samples were typically adjusted to 120 mg/dL glucose in whole blood.

TABLE 3

| No. | Compound | Max. K/S | % K/S | 60s K/S | % drift |
| --- | --- | --- | --- | --- | --- |
| 1 | ANS | 2.318 | 100 | 1.7 | 26.66 |
| 2 | 4'-tert-butyl ANS | 2.978 | 128 | 2.704 | 9.20 |
| 3 | 4'-isopropyl ANS | 2.949 | 127 | 2.634 | 10.68 |
| 4 | 4'-methyl ANS | 3.032 | 131 | 2.715 | 10.46 |
| 5 | 3',5'-di-tert-butyl ANS | 2.302 | 99 | 2.144 | 6.86 |
| 6 | 2'-tert-butyl ANS | 2.814 | 121 | 2.326 | 17.34 |
| 7 | 2'-methyl ANS | 3.123 | 135 | 2.673 | 14.41 |

K/S = K/S is a measure of reflectance, discussed and defined in USP 4,935,346, col. 14, the disclosure of which is herein incorporated by reference
Max. K/S = maximum value of K/S during 2 minutes of measurement.
% K/S= [(Max K/S of analog)/(Max K/S of ANS)] × 100
60s K/S = K/S @ 660 nm taken 60 sec after application of blood to the strip
% drift = [(K/S Max-60s K/S)/(K/S max)] × 100

III. Results

It was found that when the ANS analogs of the subject invention were employed in a glucose assay as described in II, supra, reduced drift was observed in the dye product, as compared with systems in which ANS is employed. Furthermore, the color yield was increased as compared with systems in which ANS is employed. Finally, 4'-tert-butyl ANS was found to reach the completion of the reaction faster than ANS or the other ANS analogs that were tested.

It is evident from the above results and discussion that the subject invention provides a number of advantages as compared to ANS when used in a signal producing system that further includes MBTH (or analogs thereof). These advantages include reduced drift and increased color yield. Furthermore, the subject analogs are suitable for use with a broader range of MBTH analogs than is ANS. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. An 8-(anilino)-1-naphthalenesulfonate (ANS) analog which is capable of reacting with 3-methyl-2-benzothiazolinone hydrazone hydrochloride (MBTH), or an analog thereof, to produce a dye product having reduced drift as compared to the dye product produced upon reaction of ANS and MBTH or an analog thereof, wherein said ANS analog comprises at least one alkyl substituent bonded to the phenyl moiety, with the proviso that when said substituent is methyl, said substituent is not present at positions 3',4' or 5'.

2. The ANS analog according to claim 1, wherein said alkyl substituent comprises 1 to 6 carbon atoms.

3. The ANS analog according to claim 1, wherein said alkyl substituent is branched.

4. The ANS analog according to claim 1, wherein said alkyl substituent is linear.

5. A compound or the salt thereof of the formula:

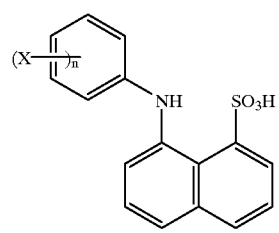

wherein:

n is 1 to 5; and

X is independently an alkyl group of from 1 to 6 carbon atoms, with the proviso that when X is at position 3', 4' or 5', X is not methyl.

6. The compound according to claim 5, wherein n is 1 or 2.

7. The compound according to claim 5, wherein said alkyl group is linear.

8. The compound according to claim 5, wherein said alkyl group is branched.

9. The compound according to claim 5, wherein said alkyl group is methyl, isopropyl or tert-butyl.

10. A compound or the salt thereof of the formula:

wherein:

n is 1 or 2; and

X is independently an alkyl moiety selected from the group consisting of methyl, isopropyl and tert-butyl, with the proviso that when X is at position 3', 4' or 5', X is not methyl.

11. The compound according to claim 10, wherein n is 1.

12. The compound according to claim 11, wherein X is 2' methyl.

13. The compound according to claim 11, wherein X is 4' tert-butyl.

14. The compound according to claim 11, wherein X is 4' isopropyl.

15. The compound according to claim 11, wherein X is 2' tert-butyl.

16. The compound according to claim 10, wherein n is 2.

17. The compound according to claim 16, where a first X is 3' tert-butyl and a second X is 5' tert-butyl.

18. A reaction product produced by the reaction of an 8-(anilino)-1-naphthalenesulfonate (ANS) analog having at least one non-hydrogen substituent on its phenyl moiety and 3-methyl-2-benzothiazolinone hydrazone hydrochloride (MBTH) or an MBTH analog, wherein said reaction product has a reduced drift as compared to the reaction product produced upon reaction of ANS and MBTH or the MBTH analog.

19. The reaction product according to claim 18, wherein said substituent of said ANS analog is an alkyl group.

20. The reaction product according to claim 19, wherein said reaction product is a reaction product of said ANS analog and MBTHSB.

21. A compound produced upon reaction of MBTH or an analog thereof with an ANS analog in the presence of oxygen, an oxidizing agent and a peroxidase, wherein said ANS analog has the structural formula:

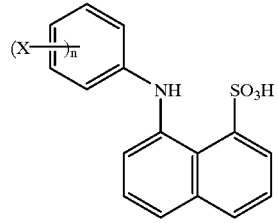

wherein:
n is from 1 to 5; and
X is independently a substituent other than H.

22. The compound according to claim 21, wherein X is an alkyl group.

23. The compound according to claim 22, wherein said alkyl group is from 1 to 6 carbon atoms.

24. The compound according to claim 23, wherein said alkyl group is methyl, isopropyl or tert-butyl.

25. A composition of matter comprising a reaction product according to claim 18.

26. The composition of matter according to claim 25, wherein said reaction product is present on a porous substrate.

27. The composition of matter according to claim 26, wherein said porous substrate is a strip.

28. A composition of matter comprising:
MBTH or an analog thereof; and
an ANS analog or the salt thereof of the formula:

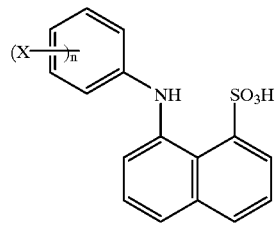

wherein:
n is from 1 to 5; and
X is independently a substituent other than H.

29. The composition of matter according to claim 28, wherein said ANS analog and MBTH or analog thereof are present on a porous substrate.

30. The composition of matter according to claim 29, wherein said porous substrate is a strip.

31. The composition of matter according to claim 29, wherein said composition of matter further comprises an oxidase and a peroxidase.

32. A method of producing a chromogenic reaction product, said method comprising:
reacting a compound or the salt thereof of the formula:

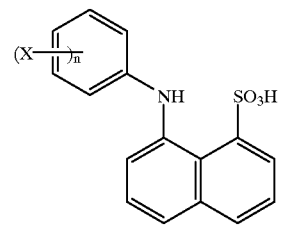

wherein
n is 1 to 5; and
X is a substituent other than H;
with
MBTH or an analog thereof in the presence of oxygen, hydrogen peroxide and a peroxidase.

33. The method according to claim 32, wherein n is 1 to 2.

34. The method according to claim 32, wherein X is an alkyl group of from 1 to 6 carbon atoms.

35. In a method for detecting the presence of an analyte in a sample in which a dye couple comprising MBTH or an analog thereof and a second dye compound are employed, the improvement comprising:
employing as said second dye compound a compound or the salt thereof of the formula:

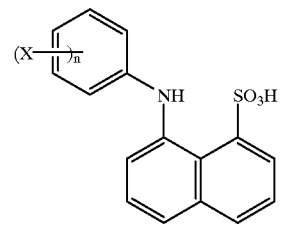

wherein
n is 1 to 5; and
X is a substituent other than H.

36. The method according to claim 35, wherein said X is an alkyl group of from 1 to 6 carbon atoms.

37. The method according to claim 35, wherein n is 1 or 2.

38. The method according to claim 35, wherein said analyte is glucose.

* * * * *